United States Patent [19]

Cesark et al.

[11] 4,403,792

[45] Sep. 13, 1983

[54] NOVEL GLYCOLIC ACID ESTERS AND AMIDES OF BIS(P-DISUBSTITUTEDAMINOPHENYL)-CARBINOL

[75] Inventors: Frank F. Cesark, Bridgewater; Robert J. Manfre, Somerville; Daniel W. Thomas, Bridgewater, all of N.J.

[73] Assignee: American Cyanamid Company, Stamford, Conn.

[21] Appl. No.: 362,367

[22] Filed: Mar. 26, 1982

Related U.S. Application Data

[62] Division of Ser. No. 256,353, Apr. 22, 1981, Pat. No. 4,343,939.

[51] Int. Cl.³ .......................... B41L 1/20; B41M 5/00
[52] U.S. Cl. .................................. 282/27.5; 427/151; 427/150; 428/320.4; 428/320.6
[58] Field of Search ................ 427/151; 544/162, 165; 560/36; 564/163, 167, 168; 260/465 D; 282/27.5; 428/320.4, 320.6

[56] References Cited

U.S. PATENT DOCUMENTS 4,115,450 9/1978 Garner et al. ........................ 564/168
4,291,902 9/1981 Burri ................................... 427/151

Primary Examiner—Norman Morgenstern
Assistant Examiner—Janyce A. Bell
Attorney, Agent, or Firm—Bruce F. Jacobs; Charles J. Fickey

[57] ABSTRACT

Glyolic acid esters and amides of bis(p-disubstitutedaminophenyl)carbinols are disclosed as color formers for use in transfer sets.

6 Claims, No Drawings

NOVEL GLYCOLIC ACID ESTERS AND AMIDES OF BIS(P-DISUBSTITUTEDAMINOPHENYL)CARBINOL

This is a division of application Ser. No. 256,353, filed Apr. 22, 1981, now U.S. Pat. No. 4,343,939.

The present invention relates to novel color former compounds which are glycolic acid esters or amides of bis(p-dialkylaminophenyl)carbinols, and to pressure-sensitive or heat-sensitive copying materials containing them as part of their color-reactant system.

Considerable investigation has been directed over the past years to the development of color former compounds for pressure-sensitive or heat-sensitive copying materials. Many of these have been various derivatives of the aforementioned bis(p-dialkylaminophenyl)carbinols. Research continues in the effort to discover improved color former compounds, that is, those having greater intensity, which exhibit limited or no "ghosting" (multiple imaging caused by sublimation), which are less expensive, and the like.

The present invention provides novel color former compounds which exhibit excellent color intensity and generally limited or no "ghosting" and which are relatively easy to make.

In accordance with the present invention, improved copying materials are obtained by the incorporation into the color-reactant system thereof of a color former compound represented by Formula (1):

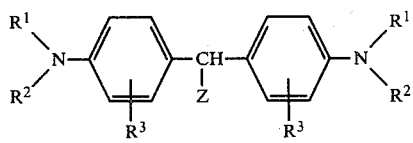

wherein $R^1$ and $R^2$, which may be the same or different, represent hydrogen, alkyl ($C_1$–$C_4$), which may be substituted by a nitrile, hydroxyl or alkoxy ($C_2$–$C_8$) group, phenyl or alkyl ($C_1$–$C_4$) substituted phenyl, benzyl or alkyl ($C_1$–$C_4$) substituted benzyl; $R^3$ represents hydrogen, or alkyl ($C_1$–$C_5$); and Z represents an ester or amide group of Formula (2) or (3), respectively:

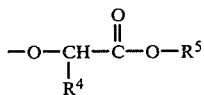

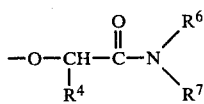

in which $R^4$ represents hydrogen, alkyl ($C_1$–$C_5$), phenyl or alkyl ($C_1$–$C_4$) substituted phenyl, or benzyl or (alkyl $C_1$–$C_4$) substituted benzyl; $R^5$ represents alkyl ($C_1$–$C_{12}$), either in a straight or branched chain, which chain may be interrupted by a hetero atom, phenyl or alkyl ($C_1$–$C_4$) substituted phenyl, benzyl or (alkyl $C_1$–$C_4$) substituted benzyl; $R^6$ and $R^7$, which may be the same or different, represent hydrogen, alkyl ($C_1$–$C_{12}$), which may be in a straight or branched chain, which chain may be interrupted by a hetero atom, phenyl or alkyl ($C_1$–$C_4$) substituted phenyl, benzyl or alkyl ($C_1$–$C_4$) substituted benzyl, or wherein $R^6$ and $R^7$, taken together with the nitrogen atom to which they are attached, combine to form a heterocyclic ring.

Preferred compounds of the invention are those wherein $R^1$ and $R^2$ are each methyl or ethyl. Most preferred compounds are those wherein $R^1$ and $R^2$ are each ethyl and $R^4$ is hydrogen or phenyl.

The compounds may readily be prepared by conventional methods known in the art, such as by the acid-catalyzed condensation of the appropriate bis(p-dialkylaminophenyl)carbinol, or lower alkyl ether thereof, with the appropriate glycolic acid ester, substituted glycolic acid ester, glycolic acid amide, or substituted glycolic acid amide. The condensation is conducted under refluxing conditions in a suitable organic solvent, with removal of water or lower alcohol.

Suitable solvents for the condensation reaction are those conventionally used for similar condensations and they include, but are not limited to, tetrahydrofuran, dioxane, n-hexane, toluene, methyl ethyl ketone, and the like, as well as mixtures thereof.

Suitable acid catalysts include, for example, methanesulfonic acid, p-toluenesulfonic acid, glacial acetic acid, and the like.

The compounds of the invention are useful color formers when brought into contact with an acid co-reactant substance that is electron accepting, for example, attapulgus clay, silton clay, silica, bentonite, halloysite, aluminum oxide, aluminum phosphate, kaolin, or any acidic clay, or an acid-acting polymer such as a phenol-formaldehyde resin, or a maleic acid rosin, partially or wholly hydrolyzed polymer of maleic anhydride with styrene, ethylene, vinyl methyl ether, or carboxy polymethylenes. Preferred acid co-reactants are attapulgus clay, silton clay, silica, and a phenol-formaldehyde polymer.

The compounds are used in pressure-sensitive or heat-sensitive copying and recording materials, which comprise, for instance, at least one pair of sheets containing a color former compound and an acidic co-reactant substance. The color former compound is desirably dissolved in an organic solvent and is preferably contained in a pressure-rupturable microcapsule.

When the microcapsules containing the color former are ruptured by pressure from, for example, a pencil, and the color former solution is thus transferred onto an adjacent sheet coated with a substance capable of acting as an electron acceptor, a colored image is produced.

The general art of making microcapsules is well-known; see, for example, U.S. Pat. Nos. 2,183,053; 2,797,201; 2,800,457; 2,800,458; 2,964,331; 3,016,308; 3,171,878; 3,265,630; 3,405,071; 3,418,250; 3,418,656; 3,424,827; and 3,427,250.

Preferably, the color formers are encapsulated dissolved in an organic solvent. Suitable solvents are preferably non-volatile, for example, polyhalogenated diphenyl, such as trichlorodiphenyl, and its mixture with liquid paraffin, tricresylphosphate, di-n-butylphthalate, dioctylphthalate, trichlorobenzene, nitrobenzene, trichloroethylphosphate, petroleum ether, hydrocarbon oils, alkylated derivatives of naphthalene, or diphenyl, terphenyls, partially hydrogenated condensed aromatic hydrocarbons. The encapsulating material may be gelatine; see U.S. Pat. No. 2,800,457. Alternatively, the capsules may be made from an aminoplast or modified aminoplast, as described in British Pat. Nos. 989,264 or 1,156,725.

A preferred copying material set may be made by coating the backside of a transfer sheet with the encapsulated color former compound and the front side of a receiving or absorbent sheet with the electron-accepting substance. Pressure-sensitive copying materials are described in U.S. Pat. Nos. 3,516,846; 2,730,457; 2,932,582; 3,427,180, 3,418,250; and 3,418,656.

The microcapsules are preferably fixed to the carrier sheet by means of a suitable adhesive. Since paper is the predominant carrier material, these adhesives are paper-coating agents, such as gum arabic, polyvinylalcohol, hydroxymethyl cellulose, casein, methyl cellulose or dextrin.

The compounds of the invention may also be used in a thermo-reactive copying material, as described, for example, in U.S. Pat. No. 4,238,130.

The following examples provide further illustration of the invention. All parts and percents are by weight unless otherwise indicated.

EXAMPLE 1

Bis(p-dimethylaminophenyl)Methoxy Acetic Acid, Ethyl Ester

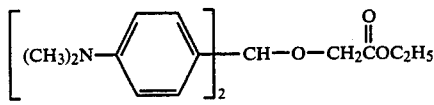

A solution of 4,4'-bis(N,N-dimethylamino)benzhydrol, methyl ether (11.0 g, 0.039 mole), ethyl glycolate 4.04 g, 0.039 mole), 70 ml of tetrahydrofuran, 230 ml of n-hexane and one drop of methanesulfonic acid was refluxed for 2 hours. On completion of the reaction, 2 drops of tetramethylguanidine was added to discharge the blue color. The reaction mixture was filtered hot and the filtrate was cooled. An oily layer formed which was removed and stripped free of solvent; the remaining filtrate was also stripped, leaving an oil. Both samples of oil were combined and chilled. A waxy solid formed which, on repeated trituration with petroleum ether, gave a white solid. Recrystallization from a mixture of petroleum ether/acetone gave a white solid, mp 63°-67.5° C.

EXAMPLE 2

2-Bis(p-dimethylaminophenyl)Methoxy Acetanilide

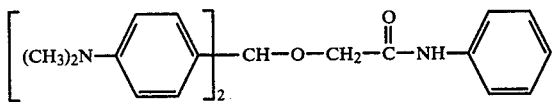

A solution of alpha-hydroxyacetanilide (3.62 g, 0.024 mole), 4,4'-bis(N,N-dimethylamino)benzhydrol, methyl ether (6.81 g, 0.024 mole) 50 ml of tetrahydrofuran, 153 ml of n-hexane, and one drop of methanesulfonic acid was refluxed for 11 hours, during which time an additional 300 ml of solvent was added. The blue-green solution was decolorized with 4 drops of tetramethylguanidine and the reaction mixture was filtered hot and the filtrate chilled. Yellow-green crystals formed, which were recrystallized from 30 ml petroleum ether/15 ml acetone to give a white solid, mp 118°-128° C.

EXAMPLE 3

Bis(p-dimethylaminophenyl)methoxyphenyl Acetic Acid, Methyl Ester

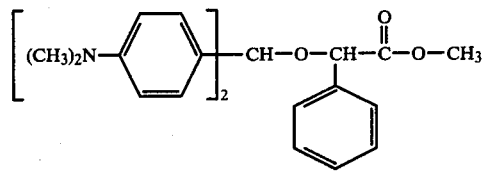

A solution of methyl mandelate (97%, 6.44 g, 0.039 mole), 4,4'-bis(N,N'-dimethylamino)benzhydrol, methyl ether (11.0 g, 0.039 mole), 70 ml of tetrahydrofuran, 240 ml of n-hexane, 3 drops of methanesulfonic acid and 10 drops of acetic acid was refluxed for 6 hours, during which time an additional 200 ml of solvent was added. The volume was reduced to 200 ml, and decolorized with tetramethylguanidine and filtered hot. The filtrate was stripped, leaving a light blue clear oil. The oil was dissolved in toluene and chilled, yielding a white solid (2.8 g, mp 102°-105° C.).

EXAMPLE 4

4-[[Bis(p-dimethylaminophenyl)methoxy]acetyl]Morpholine

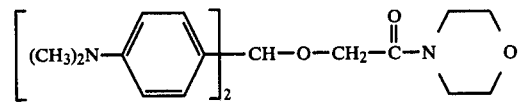

A solution of 4,4'-bis(N,N-dimethylamino)benzhydrol, methyl ether (9.0 g, 0.032 mole), glycol morpholinamide (4.6 g, 0.032 mole), 150 ml of tetrahydrofuran, 250 ml of n-hexane and 4 drops of methanesulfonic acid was refluxed for about 8 hours, during which time an additional 200 ml of solvent was added. The volume was reduced to 200 ml and the color was discharged with tetramethylguanidine. The solution was filtered hot and then cooled to precipitate a white solid. The solid was recrystallized from 350 ml of methyl cyclohexane to give 4.9 g of blue crystals; mp 147.8°-150° C.

EXAMPLE 5

Bis(p-dimethylaminophenyl)Methoxy Acetic Acid 2-Ethoxy Ethyl Ester

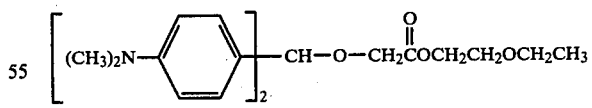

A solution of 4,4'-bis(N,N-dimethylamino)benzhydrol, methyl ether (11.0 g, 0.039 mole), 2-ethylhexyl glycolate (5.91 g, 0.039 mole), 90 ml of tetrahydrofuran, 200 ml of n-hexane and 4 drops of methanesulfonic acid was refluxed for about 11 hours, replacing solvent (60/40-hexane/tetrahydrofuran) as distillate was removed; then, 4 drops of tetramethylguanidine was added to discharge the color, the mixture was filtered hot and then cooled to about −30° C. A white precipitate formed which was filtered and washed with cold hexane. The product was recrystallized from 50 ml of methyl cyclohexane to give 5 g of product, mp 60.0°-61.8° C.

EXAMPLE 6

Bis(p-dimethylaminophenyl)Methoxy Acetic Acid, Benzyl Ester

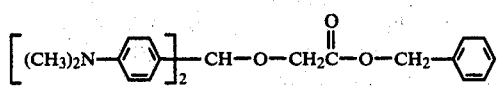

A solution of 4,4'-bis(N,N-dimethylamino)benzhydrol, methyl ether (11.0 g, 0.039 mole), benzyl glycolate (6.6 g, 0.039 mole), 90 ml of tetrahydrofuran, 200 ml of hexane, and 10 drops of methanesulfonic acid was refluxed for 6 hours, replacing solvent as distillate was removed; then, 10 drops of tetramethylguanidine was added to discharge the color and the reaction mixture was filtered hot and cooled. A white solid formed which was filtered, washed with petroleum ether and then recrystallized from 4/1 hexane/acetone. The resulting white crystalline product had a mp 101.8°-103° C.

EXAMPLE 7

2-[Bis(p-dimethylaminophenyl)methoxy]-N-methylacetamide Ester

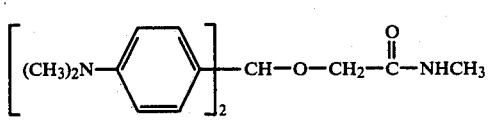

A solution of 3.6 g, 0.04 mole, of methyl glycolamide, 10 g, 0.038 mole, of 4,4'-bis(N,N-dimethylamino)benzhydrol, 75 ml of dioxane, 100 ml of toluene, and 3 ml of acetic acid was refluxed until the theoretical amount of water was removed. The reaction mixture was washed with dilute ammonium hydroxide and then dried over sodium sulfate. The solution was concentrated to a volume of 50 ml, cooled, and the resulting white solid filtered. The product was recrystallized from toluene to give white crystals, mp 134°-135° C.

Following the above procedure except for the use of 3.0 g, 0.04 mole, of glycolamide instead of methyl glycolamide, there was obtained 4,4'-bis(N,N-dimethylamino)benzhydrol, glycolamide, mp 171°-173° C.

EXAMPLE 8

Bis(p-diethylaminophenyl)Methoxy Acetic Acid, Benzyl Ester

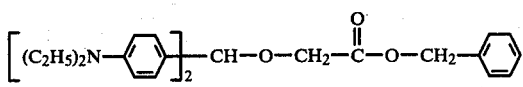

A solution of 11 g, 0.034 mole, of 4,4'-bis-(N,N-diethylamino)benzhydrol, 6 g, 0.034 mole, of benzyl glycolate, 60 ml of methyl ethyl ketone, 150 ml of n-hexane and 3 drops of methanesulfonic acid was refluxed for 1.5 hours, replacing distillate with solvent as the water was removed; then, 4 drops of tetramethylguanidine was added to dispel the color, the mixture was filtered hot and cooled in dry ice bath to −40° C. A yellow, gummy precipitate formed, which was washed with cold n-hexane. The precipitate was redissolved in 150 ml of petroleum ether, heated to 35° C. and cooled. The gummy precipitate remained. The mother liquor was decanted, decolorized with charcoal at 35°-40° C., and filtered. On cooling to 0° C., a white solid precipitated, which was filtered, washed with petroleum ether and dried; mp 62°-63.5° C.

The above procedure was repeated except that ethyl glycolate was used instead of benzyl glycolate. There was obtained 4,4'-bis(N,N-diethylamino)benzhydrol, ethyl glycolate, mp 45°-52° C.

EXAMPLE 9

Bis(p-diethylaminophenyl)Methoxy Acetanilide

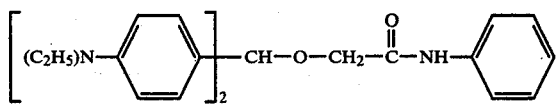

A solution of 4,4'-bis(N,N-diethylamino)benzhydrol (11.0 g, 0.034 mole), glycolanilide (5.1 g, 0.034 mole), 37.5 ml of methyl ethyl ketone, 112.5 ml of n-hexane, and 7 drops of methanesulfonic acid was refluxed for about 2 hours, removing water as formed. The solution was then treated with 5 drops of tetramethyl-guanidine and filtered hot. On cooling, the filtrate yielded a tan precipitate. The precipitate was filtered, washed with n-hexane, and dried. The pale yellow solid was recrystallized from 80 ml of methylcyclohexane and 450 ml of acetone to give a solid product, mp 123°-125° C.

EXAMPLE 10

4'Chloro-2-[bis(p-dimethylaminophenyl)methoxy]acetanilide

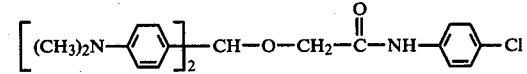

A solution of 4,4'-bis(N,N-dimethylamino)benzhydrol, methyl ether, (8.0 g, 0.028 mole), p-chloroglycolanilide (5.23 g, 0.028 mole), 170 ml of tetrahydrofuran, 120 ml of n-hexane, and 4.5 ml of glacial acetic acid was refluxed for about 8.5 hours, replacing solvent as distillate was removed. Color was then discharged by the addition of 20 drops of tetramethylguanidine and the solution was filtered hot. Hexane was added to the filtrate, yielding a light green oil. The oil was removed and the hexane solution, on cooling, gave a light blue solid. The solid was filtered, washed with petroleum ether and dried. Recrystallization from 150 ml methylcyclohexane/40 ml acetone gave a yellow-white, gummy solid. This was recrystallized from VM&P naphtha to give a fine white powder, mp 137.5°-140° C.

EXAMPLE 11

To determine the effectiveness of the compounds herein as color formers, and to compare them against Crystal Violet Lactone and some compounds according to formula (1) above wherein Z is

as in U.S. Pat. No. 3,995,088, the following tests were performed:

Measurement of Image Intensity

A 220-screen quadragravure hand roller is used to evenly apply a 0.5% xylene solution of the color former to resin coated color former paper. The visible reflectance spectrum is obtained with a General Electric-Hardy spectrophotometer. The λmax spectral value is transformed using Kebulka-Munk Theory to "k/s," reflectance for "infinitely thick " sample. The value obtained is compared with a Crystal Violet Lactone (CVL) image value of 1.6. At least one CVL sample is included in each test series as a control. Reproducibility for the method has averaged 5% with 13% maximum deviation. Data for compounds are given in Table I.

Sublimation (Ghosting) Test Method

Ghosting observations are made by applying 5 drops of a 0.5% xylene solution of the color former compound to a 220-screen quadragravure hand roller, and then evenly applying the solution to Reeve Angel filter paper (#201). The approximately 2"×4" center section of the drawdown is cut out. The solution side of the filter paper is placed in contact with the active side of resin coated color former paper and the two sheets are placed in an Atlas Scorch Tester (ST-469, type SO-5A) and heated for 16 hours at 145°–150° F. The extent of color formed on the color former sheet is then visually estimated. Ghosting results for the compounds are given in Table I.

TABLE I

Color Intensity and Sublimation of Color Former Compounds

| Compound | Example No. | Image Intensity | Sublimation |
|---|---|---|---|
| Crystal Violet Lactone | — | 1.6 | None |
| [MB]$_2$CHOCH$_3$ | — | 1.87 | Heavy |
| [MB]$_2$—CHOCH(CH$_3$)$_2$ | — | 1.31 | Heavy |
| [MB]$_{\overline{2}}$CHOCH$_2$—C$_6$H$_5$ | — | 1.30 | Heavy |
| [MB]$_{\overline{2}}$CHOCH$_2$COCH$_2$CH$_3$ | 1 | 2.47 | Mod. - Considerable |
| [MB]$_{\overline{2}}$CHOCH$_2$CNH—C$_6$H$_5$ | 2 | 2.27 | Sl. - Moderate |
| [MB]$_{\overline{2}}$CHO—CH(C$_6$H$_5$)—COCH$_3$ | 3 | 1.95 | Slight |
| [MB]$_{\overline{2}}$CHOCH$_2$—C(O)—N(morpholino) | 4 | 1.91 | Sl. - Moderate |
| [MB]$_{\overline{2}}$CHOCH$_2$COCH$_2$CH$_2$OCH$_2$CH$_3$ | 5 | 2.44 | Sl. - Moderate |
| [MB]$_{\overline{2}}$CHOCH$_2$COCH$_2$—C$_6$H$_5$ | 6 | 2.38 | Slight |
| [MB]$_{\overline{2}}$CHOCH$_2$C(O)—NHCH$_3$ | 7 | 2.54 | Considerable |
| [MB]$_{\overline{2}}$CHOCH$_2$C(O)—NH$_2$ | 7 | 2.42 | Mod. Considerable |
| [MB]$_{\overline{2}}$CHOCH$_2$C(O)—NH—C$_6$H$_4$—Cl | 10 | 2.14 | Moderate |
| [EMB]$_{\overline{2}}$COCH$_2$COCH$_2$—C$_6$H$_5$ | 8 | 2.14 | None - Trace |
| [EMB]$_{\overline{2}}$CHOCH$_2$COCH$_2$CH$_3$ | 8 | 2.22 | None - Trace |

TABLE I-continued

Color Intensity and Sublimation of Color Former Compounds

| Compound | Example No. | Image Intensity | Sublimation |
|---|---|---|---|
| 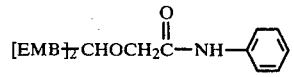 | 9 | 2.19 | Trace |

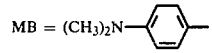

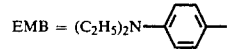

What is claimed is:

1. A pressure-sensitive transfer copy set comprising a transfer sheet superimposed on an absorbent sheet, the transfer sheet having a coating on the surface thereof in contact with said absorbent sheet; said coating comprising a color former compound represented by the Formula (1):

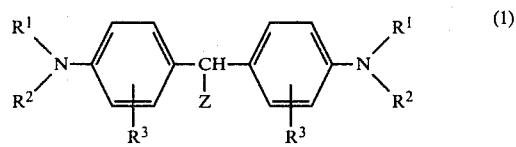

wherein $R^1$ and $R^2$, which may be the same or different, represent hydrogen, alkyl containing from about 1 to 4 carbon atoms, which may be substituted by a nitrile, hydroxyl or a 2 to 8 carbon alkoxy group, phenyl or alkyl ($C_1$–$C_4$) substituted phenyl, benzyl or alkyl ($C_1$–$C_4$) substituted benzyl; $R^3$ represents hydrogen or alkyl containing about 1 to 5 carbon atoms; and Z represents an ester or amide group represented by Formula (2) and (3), respectively:

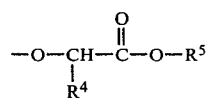

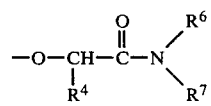

wherein $R^4$ represents hydrogen, alkyl containing about 1 to 5 carbon atoms, phenyl or alkyl ($C_1$–$C_4$) substituted phenyl, or benzyl or alkyl ($C_1$–$C_4$) substituted benzyl; $R^5$ represents alkyl containing about 1 to 12 carbon atoms, either in a straight or branched chain, which chain may be interrupted by a hetero atom, phenyl or alkyl ($C_1$–$C_4$) substituted phenyl, or benzyl or alkyl ($C_1$–$C_4$) substituted benzyl; $R^6$ and $R^7$, which may be the same or different, represent hydrogen, alkyl containing about 1 to 12 carbon atoms in either a straight or branched chain, which chain may be interrupted by a hetero atom, phenyl or alkyl ($C_1$–$C_4$) substituted phenyl, benzyl, or alkyl ($C_1$–$C_4$) substituted benzyl, or wherein $R^6$ and $R^7$, taken together with the nitrogen atom to which they are attached, combine to form a heterocyclic ring, which forms a colored image when brought into contact with an electron acceptor, and a material normally insulating said color former compound in said coating to prevent contact with said absorbent sheet but being rupturable upon the application of pressure on said transfer sheet, whereby said color former compound is released and contacts said absorbent sheet; said absorbent sheet having a coating on a surface thereof in contact with said transfer sheet, said coating containing an electron acceptor.

2. The transfer copy set of claim 1 wherein $R^1$ and $R^2$ of Formula (1) are both methyl or ethyl groups.

3. The transfer copy set of claim 1 wherein $R^1$ and $R^2$ of Formula (1) are ethyl and $R^4$ is hydrogen or phenyl.

4. The transfer copyset of claim 1 wherein the coating on said absorbent sheet comprises an acid-actng phenolic resin.

5. The transfer copyset of claim 1 wherein the coating on said absorbent sheet comprises an acid-acting clay.

6. The transfer copyset of claim 3 wherein said transfer sheet and said absorbent sheet are paper.

* * * * *